United States Patent [19]

Kuypers et al.

[11] Patent Number: 5,134,057
[45] Date of Patent: Jul. 28, 1992

[54] METHOD OF PROVIDING A SUBSTRATE WITH A LAYER COMPRISING A POLYVINYL BASED HYDROGEL AND A BIOCHEMICALLY ACTIVE MATERIAL

[75] Inventors: Martinus H. Kuypers, Riethoven; Gerardus F. J. Steeghs, Geldrop; Egbert Brinkmann, Enschede, all of Netherlands

[73] Assignee: 501 PPG Biomedical Systems, Inc., Pittsburgh, Pa.

[21] Appl. No.: 419,310

[22] Filed: Oct. 10, 1989

[30] Foreign Application Priority Data

Oct. 10, 1988 [EP] European Pat. Off. ........ 88116789.4

[51] Int. Cl.$^5$ .................. G03F 7/30; G03F 7/016; C08B 37/10; A61F 2/00
[52] U.S. Cl. .................... 430/325; 430/175; 430/176; 424/423; 536/21; 523/112
[58] Field of Search ........ 430/175, 176, 325; 536/21; 424/78, 80, 140, 423

[56] References Cited

U.S. PATENT DOCUMENTS

| | | | |
|---|---|---|---|
| 3,189,451 | 6/1965 | Reichel | 430/175 |
| 3,673,612 | 7/1972 | Merrill et al. | 424/82 |
| 3,810,781 | 5/1974 | Eriksson et al. | 424/423 |
| 4,008,208 | 2/1977 | Lednicer et al. | 424/78 |
| 4,118,485 | 10/1978 | Eriksson et al. | 536/21 |
| 4,239,664 | 12/1980 | Teng et al. | 424/80 |

FOREIGN PATENT DOCUMENTS

| | | |
|---|---|---|
| 0149693 | 7/1985 | European Pat. Off. . |
| 45-9614 | 9/1966 | Japan ........................ 430/176 |
| 57-146247 | 10/1980 | Japan ........................ 430/176 |
| WO 83/00750 | 3/1983 | PCT Int'l Appl. . |

OTHER PUBLICATIONS

Tsunoda and Yamaoka, Study of the Crosslinking of Polyvinyl Alcohol by Light-Sensitive Tetrazonoium Salt.
Chemical Abstract 80060b, vol. 99.
Chemical Abstract 214126f, vol. 105.

*Primary Examiner*—Richard L. Schilling
*Assistant Examiner*—John S. Y. Chu
*Attorney, Agent, or Firm*—McGlew & Tuttle

[57] ABSTRACT

Disclosed is a method of providing a substrate with a layer comprising a polyvinyl base hydrogel and a biochemically active material by photolithograhy, comprising coating the substrate by centrifugal force with an aqueous solution of a photosensitive hydrogel forming polymer, a crosslinking agent and a biochemically active material, drying said coating, exposing the coated substrate through a photomask to ultraviolet radiation and developing said exposed coating, which is characterized by applying to the substrate an aqueous solution comprising as the cross-linking agent a polyazonium compound and glutardialdehyde. Because of this specific combination of cross-linking agents superior properties with respect to the binding of the biochemically active material are obtained.

19 Claims, 3 Drawing Sheets

METHOD OF PROVIDING A SUBSTRATE WITH A LAYER COMPRISING A POLYVINYL BASED HYDROGEL AND A BIOCHEMICALLY ACTIVE MATERIAL

The invention relates to a method of providing a substrate with a layer comprising a polyvinyl based hydrogel and a biochemically active material by photolithography, comprising coating the substrate with an aqueous solution of a photosensitive hydrogel forming polymer, a crosslinking agent and a biochemically active material, drying said coatings, exposing the coated substrate through a photomask to ultraviolet radiation and developing said exposed coating.

BACKGROUND OF THE INVENTION

Sensor-catheters used as an indwelling catheter can be used to monitor physiological values such as pressure, oxygen, pH etc., over some period of time. During a long contact-time, the blood can clot on the surfaces of the sensor-catheter. This clotting is caused by the cascadic biochemical mechanism of the blood, forming a deposit called thrombus. This generation of thrombi can be initiated by the bio-incompatibility of a foreign surface because of the chemical, physical and mechanical properties of the surface. The formation of thrombi is not only caused by properties of the foreign surface but also by a collision of a blood platelet with the foreign surface irritating the biochemical behavior of that platelet which can result in the formation of a thrombus in a remote part of the blood circulation system. It is important to control this biochemical reaction to avoid thrombogeneration which can lead to embolism or can at least impair the functionality of the sensor-catheter. In many cases the monitoring with a sensor-catheter will be done during a short time, e.g., during catheterization for diagnostical purposes. In those cases the thrombogenic processes can be controlled by the administration of anti-coagulantia, of which heparin is the most widely used. However, heparin administration during a longer period of time can lead to adverse effects, e.g. to osteoporosis (softening of the bone tissue) and to the so-called "heparin rebound effect" in which heparin activity returns somewhere in the bloodstream some hours after its neutralization. During monitoring in the vascular system of the newborn baby, the heparin can initiate further problems in the instable metabolism of the baby.

As is known from a reviewing article ("Heparinised polymers as thromboresistant biomaterials" published by J. E. Wilson in Polym. plat. Technol. Eng(16(2) 119-208 (1981)), several trials have been made to bind heparin to the surfaces of medical devices which shall be introduced into the bloodstream. In the literature there is still a controversial dispute about the activity and the antithrombogenic mechanism of heparin.

According to the review by J. E. Wilson (see above), the anti-thrombogenity may be caused by the leaching of heparin from the polymer. The microatmosphere of the dissolved heparin around the device causes the anti-thrombogenity.

The covalent binding of heparin to a polymer results in a decrease of its activity. However, M.F.A. Goosen and M. V. Sefton ("Properties of a heparin-poly(-vinylalcohol)-hydrogel coating" published in the Journal of Biomed. Mat. Res., Vol. 17, 359-373 (1983)), showed that chemical binding of heparin to polyvinyl alcohol positively affects the anti-thrombogenity of the polymer. The could prove that no heparin leached out from the P.V.A. hydrogel during their biological activity measurements.

Subject matter of the European Patent 0 149 693 is a method of forming on medical devices an anti-thrombogenic layer comprising a hydrogel forming polymer, e.g. polyvinyl alcohol, and heparin, which is characterized by the steps of a) preparing an aqueous solution of photosensitive hydrogel forming polymer such as polyvinyl alcohol or polyvinylpyrrolidone, a cross-linking agent, and heparin; b) coating the medical device with said solution; and c) exposing the coated device to ultraviolet radiation.

This new method is easy to perform and relies on the well-known principles of lithography and allows for the manufacture of antithrombogenic layers on semiconductor or electrically conducting surfaces specifically usable for the manufacture of sensors, catheters or other medical instruments.

It is further known from an article by T. Tsunoda and Y. Yamaoka (J. of Applied Polymer Science, Vol. 8 (1964), pp. 1379-1390) that polyvinyl alcohol can be crosslinked by light-sensitive tetrazonium salts.

It has now surprisingly been found that by far better results than those described in the above European Patent 0 149 693 can be obtained not only during the formation of anti-thrombogenic layers but of layers comprising a biochemically active material on a substrate surface in case this layer is deposited using a specific combination of crosslinking agents, i.e. a polyazonium compound in combination with glutardialdehyde.

SUMMARY OF THE INVENTION

The subject matter of the present invention, therefore, is a method of providing a substrate with a layer comprising a polyvinyl based hydrogel and a biochemically active material by photolithography, comprising coating the substrate by centrifugal force with an aqueous solution of a photosensitive hydrogen forming polymer, a crosslinking agent and a biochemically active material, drying said coating, exposing the coated substrate through a photomask to ultraviolet radiation and developing said exposed coating by dissolving the non crosslinked areas of the coating. The aqueous solution applied to the substrate uses as the crosslinking agent a polyazonium compound and glutardialdehyde.

By making use of this specific combination of crosslinking agents, a sufficient selective deposition of the layer by photolithography can be obtained. After exposing the coated substrate through the photomask to ultraviolet radiation, the pattern deposition will manifest itself with a sufficient resolution (<0.1 mm) after development in water. The obtained layer is semipermeable, in that it stops proteins from penetrating the hydrogel and lets only pass small biochemical molecules and electrolyte. The layer provided on the substrate is specifically characterized by a superior adherence to the substrate. When having washed out the unreacted biochemically active material from the layer, the coating shows the desired biochemical activity without giving rise to undesired effects by dissolving any of the biochemically active material. For example, when introducing heparin as the biochemically active material into the layer, the formed hydrogel layer shows anti-thrombogenity, controlled by blood-clotting tests, like the well-known recalcification test.

According to the invention it is furtheron possible to immobilize other biochemical active materials, such as proteins like enzymes, polysaccharides, such as heparin and protein matter, such as anti-bodies, hormones, etc., so that it becomes possible to use a wide variety of biochemically active materials to be used in biosensors for selective detecting purposes.

By making use by the specific combination of cross-linking agents, it is possible to provide coatings having specific properties in a reproducible way.

DETAILED DESCRIPTION OF THE INVENTION

In the method of the present invention the substrate is coated by centrifugal force with a solution comprising the hydrogel forming polymer, a biochemically active material and as a crosslinking agent a combination of a polyazonium compound and glutardialdehyde. As polyazonium compound a monomeric or polymeric organic compound comprising at least two side-chain and/or terminal diazonium salt groups is used. Preferred examples of such polyazonium compounds are those referred to in the above-noted article of T. Tsunoda and T. Yamaoka (loc. cit.) such as a benzidinetetrazonium salt, preferably benzidinetetrazonium chloride-zinc chloride double salt, a diethylbenzidinetetrazonium salt, preferably diethylbenzidinetetrazonium chloride-zinc chloride double salt or diethylbenzidinetetrazonium sulfate, a dichlorobenzidinetetrazonium salt, preferably dichlorobenzidinetetrazonium chloride-zinc chloride double salt, an n-tolidinetetrazonium salt, preferably o-tolidinetetrazonium chloride-zinc chloride double salt or o-tolidinetetrazonium sulfate, an o-dianisidine-tetrazonium salt, preferably o-dianisidinetetrazonium chloride-zinc chloride double salt or o-dianisidinetetrazonium sulfate and oligomer or polymer polyazonium compounds such as the reaction product of diphenylamine diazonium sulfate with formaldehyde obtainable by PCAS, France under the designation DTS-18.

In the method of the present invention, as the hydrogel forming polymer, polyvinyl alcohol and polyvinyl pyrrolidone are preferably used. As the polyvinyl alcohol, a hydrolyzed product having a hydrolysis degree of 87 to 100% is well suited. Specifically preferred are polyvinyl alcohols having a polymerization degree Pw of 2600 and a viscosity of 40 to 50 mPas (4% solution).

The polyvinyl pyrrolidone used in the method of the present invention is, as is the polyvinyl alcohol, a pharmaceutical acceptable product obtainable on the market.

As the biochemically active material, a protein, proteinous or polysaccharide material can be used, such as an enzyme catalyzing a biochemical reaction in which hydrogen peroxide is formed, such as glucose oxidase or alcoholase, or an enzyme catalyzing a biochemical reaction in which the pH is changed. As the polysaccharide material an anti-thrombogenic material, such as heparin may be used. It is further possible to use any other kind of enzymes or proteinous matter, such as antibodies, hormones and other chemically active material used in sensors for selectively detecting chemical or biochemical reactions.

In the method of the present invention it is preferred to coat the substrate with a solution in water or saline (for example a salty solution such as a 0.9% by weight solution of NaCl in water or an aqueous buffer solution) comprising 0.5 to 12% by weight, preferably 5 to 9% by weight and more preferably about 7% by weight of the hydrogel forming polymer, such as polyvinyl alcohol or polyvinyl pyrrolidone and, based upon 100 parts by weight of said hydrogel forming polymer in said solution, 1 to 3 and preferably 2 to 2.5 parts by weight of said polyazonium compound, 0.5 to 10 and preferably 5 to 8.5 parts by weight of glutardialdehyde and 0 to 20, preferably 2 to 10 parts by weight of heparin or 0 to 10 and preferably 2 to 4 parts by weight of glucose oxidase as an example for an enzyme.

When carrying out the method of the present invention first an aqueous or saline solution of the above-mentioned components, preferably in the amounts referred to above is prepared, thereafter the surface of the substrate is coated with said solution. By spinning the substrate a smooth and even thin coating layer is obtained. After drying, the coating is covered with a photomask having the specific pattern in which the layer is to be applied. The coated device is then subjected to ultraviolet radiation through said photomask. Following this, the coating is developed in water or an aqueous solution to dissolve the non-radiated parts of the coating, so that a local selective coating will remain.

When doing this the well-known principles of lithography can be used, such as described in detail in the book by William S. DeForest "Photoresist: Materials and Processes", McGraw-Hill, Inc. (1975).

The substrate coated with the method of the present invention preferably is part of a biochemical sensor and is made of silicon, alumina, silica, glass or another conductive, semi-conductive or non-conductive (such as polymer) material.

In some cases it is preferable to first provide the substrate with a base layer improving the semipermeability of the layer by applying a solution comprising the hydrogel forming polymer, the polyazonium compound and glutardialdehyde. When doing this, preferably a solution in water or saline (0.9% by weight of NaCl) is used comprising 0.5 to 10% by weight of said hydrogel forming polymer and, based upon 100 parts by weight of said hydrogel forming polymer, 2 to 3 parts by weight of said polyazonium compound and >0.5 parts by weight of glutardialdehyde.

The adhesion of the layer to a substrate made of a polymeric substance can be improved by chemically hydroxylizing of the polymeric surface by chemical etching in a mixture of chromic acid and sulphuric acid, resulting in the formation of C—OH, C═O, O═C—OH and $SO_3H$-groups. The polyazonium crosslinking agent used according to the invention will also react with some of these groups resulting in improving the adhesion of the polyvinyl alcohol coating comprising the biochemically active material, such as heparin to such a polymer substrate. In this way the biochemically active material is firmly bound by covalent bonds to the polyvinyl alcohol matrix and the polymeric substrate.

BRIEF DESCRIPTION OF THE DRAWINGS

In the following the present invention is further explained, making reference to the drawings herewith enclosed. In the drawings.

DETAILED DESCRIPTION OF THE DRAWING

Figure 1:
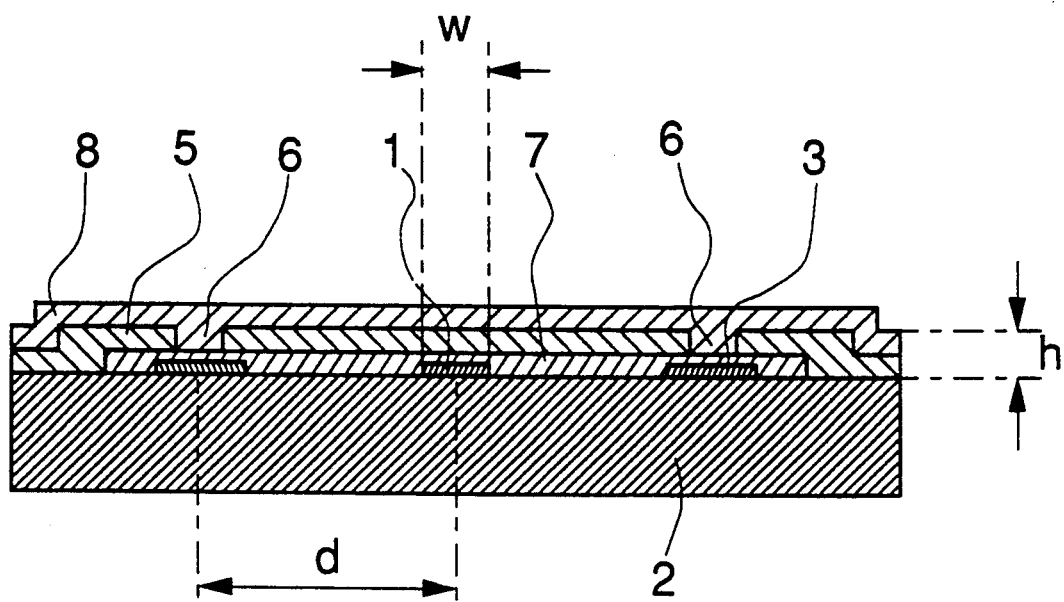
FIG. 1 shows an oxygen sensor of the Clark type manufactured in accordance with the lithographic method of the present invention.

FIG. 1 shows an oxygen sensor of the Clark type manufactured in accordance with the lithographic method of the present invention. A silicon substrate 2 supports a cathode 1 and an anode 3 which are deposited on the substrate according to the known methods for the manufacture of printed or integrated circuits. Both electrodes are covered by a layer 7 of a hydrophilic polymer which is protected on the outside by means of a membrane 5 and the hydrogel layer 8. For activating the sensor the electrolyte is derived from the biological fluid surrounding the sensor and has to be brought into contact with the electrode and the space between them. The hydrogel 8 and holes 6 within the membrane 5 permit access of the electrolyte to the hydrophilic polymer layer 7 so that the electrolyte can pass along this layer to the cathode 1 for activating the cell. Oxygen or any other gaseous constituent of the fluid under examination diffuses through membrane 5 and layer 7 to the cathode 1, therewith influencing the electrochemical process between electrodes 1 and 3. These electrodes are connected to a source of DC, and the amount of current induced by the reduction and oxidation process at the cathode and the anode, respectively, is used for determining the content of oxygen within the biological medium into which the sensor is inserted. Instead of silicon another insulating substrate such as glass, ceramics or epoxides may be used. When using the cell, it must be prevented that the direct access of oxygen through the holes 6 results in a change or increase of the oxygen diffusion through the selectively permeable membrane 5 to the electrodes. For this reason the distance d of the holes 6 from the cathode 1 is by far larger, e.g. five times larger than the width w of the active front surface area of cathode 1. The thickness h of the hydrophilic polymer layer 7 is very small, preferably less than 4 $\mu$m. Therewith most of the oxygen reaching cathode 1 therefore stems from diffusion through the membrane 5 and the oxygen portion entering through the holes 6 and traveling along the hydrophilic polymer layer 7 can be neglected. This layer may be made of a hydrogel such as polyvinyl alcohol or polyvinyl pyrrolidone, polyacryl-amide, hydroxyethyl-methacrylate or derivatives of these compounds. The cathode and anode may consist of silver. The hydrophilic polymer layer applied with the method of the invention comprises a polyvinyl alcohol hydrogel and heparin as an anti-thrombogenic substrate 8 acts as a sieve which is permeable for the electrolyte, oxygen, carbon dioxide and relatively small biological organic molecules such as glucose.

The above described construction can also be used as a glucose sensor, when the enzyme glucose-oxidase is immobilized alone or together with heparin in the hydrophilic polymer layer 8. The oxygen flux through the hydrogel polymer layer 8 is wholly or partly intercepted by the reaction

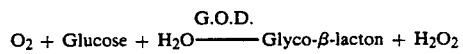

G.O.D.
$O_2$ + Glucose + $H_2O \longrightarrow$ Glyco-$\beta$-lacton + $H_2O_2$

The quantity of the oxygen is inverse to the glucose concentration.

Figure 2:
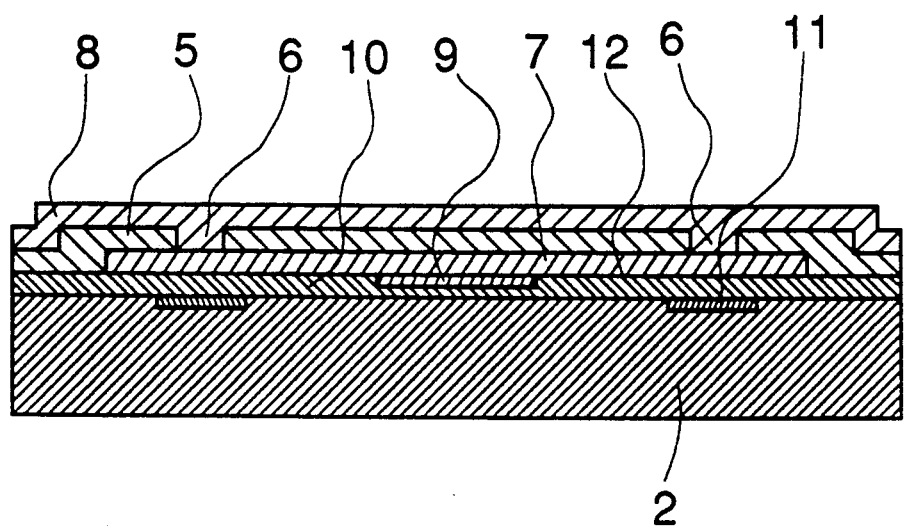
FIG. 2 shows a second embodiment of an ISFET sensor obtained according to the method of the invention.

In the embodiment shown in FIG. 2 the electrode system is replaced by an ISFET with a hydrogeion sensitive gate, preferably -$Al_2O_3$, $Ta_2O_5$ or $Si_3N_4$. As shown in FIG. 2, the ISFET comprises on a silicon substrate 2 a source 10 and a drain 11 covered by a dielectric insulating material 12 carrying the gate 9, which is covered with the layer 7 of a hydrophilic polymer which is protected on the outside by means of the membrane 5 and a hydrogel layer 8. The membrane 5 is provided with holes 6 to permit the access of the electrolyte to the hydrophilic polymer layer 7.

Figure 3:
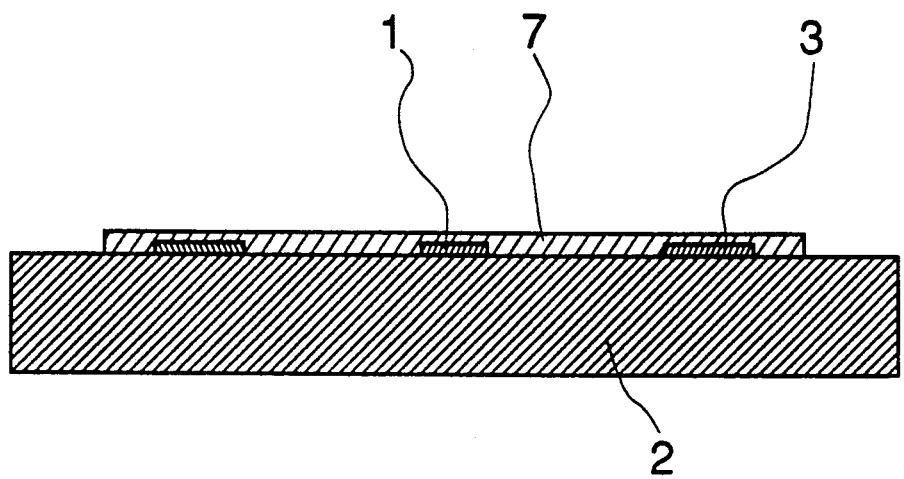
FIG. 3 shows a third embodiment of an oxygen sensor of the Clark or ISFET sensor type obtained according to the method of the present invention.

In the embodiment of FIG. 3, the semipermeable membrane layer 8 and the membrane 5 have been omitted. In the hydrogel layer 7, both the enzyme and the anti-thrombogenic active material, like heparin are bound by the method of the invention.

The following example further describes a preferred embodiment of the present invention.

EXAMPLE

By dissolving 10% by weight of polyvinyl alcohol in saline and adding 0.2% by weight of a polymeric polyazonium compound obtained by condensation of diphenylamine 4-diazonium sulfate with formaldehyde (obtained as a yellow powder having a melting point of 180° and soluble in water (DTS-18)) a stock solution is prepared. To 7 gram of this polyvinyl alcohol stock solution, a 3 g solution comprising 1.3% by weight of glutardialdehyde and 3.3% by weight of heparin are added.

The coating solution is applied as a uniform coating on a substrate by spinning (centrifugal forces) and dried. Thereafter the coating is subjected to ultraviolet light to provide a cross-linking of the polyvinyl alcohol and heated in an oven at 60° C. to provide the full cross-linking of the glutardialdehyde.

After the introduction of this layer in water for 25 hours the loose bounded heparin has been leached out and a polyvinyl alcohol/polyazonium-glutalaldehyde-heparin-membrane is obtained having a water content of 55%.

The membrane obtained is not permeable for most plasma-proteins, which can be demonstrated by the fact that albumine one of the smallest plasma proteins does not diffuse through this membrane.

Because of the covalently bound heparin and obviously the continuous leaching out of a minor quantity of heparin the membrane shows during the recalcification test superior results in comparison to silicone rubber, which is considered to be an excellent material as far as its anti-thrombogenic properties are concerned.

We claim:

1. Method of providing a substrate with a layer comprising a polyvinyl based hydrogel and a biochemically active material by photolithography, comprising combining a preformed first aqueous solution of a photosensitive hydrogel forming polymer and a polyazonium compound as a first cross linking agent with a preformed second aqueous solution of a biochemically active material and glutardialdehyde as a second cross linking agent to form a combination aqueous solution of the hydrogel forming polymer, the biochemically active material and the combination of the polyazonium compound and glutardialdehyde as cross linking agents, coating the substrate by centrifugal force with said combination aqueous solution, drying the coating, exposing the coated substrate through a photomask to ultraviolet radiation and developing the exposed coating by dissolving the non-irradiated parts to form a negative image.

2. Method of claim 1 wherein the polyazonium compound is a monomeric or polymeric organic compound comprising at least two side chain and/or terminal diazonium salt groups.

3. Method of claim 2 wherein the polyazonium compound is a member selected from the group consisting of a benzidine tetrazonium salt, a diethyl benzidine tetrazonium salt, a dichloro benzidine tetrazonium salt, an o-tolidine tetrazonium salt, an o-dianisidine tetrazonium salt and a reaction product of diphenylamine diazonium sulfate with formaldehyde.

4. Method of claim 1 wherein the hydrogel forming polymer is polyvinyl alcohol or polyvinyl pyrrolidone.

5. Method of claim 1 wherein the biochemically active material is a member selected from the group consisting of a protein, proteinous material and polysaccharide.

6. Method of claim 5 wherein the member of said group is an anti-thrombogenic material or an enzyme.

7. Method of claim 6 wherein the anti-thrombogenic material is heparin.

8. Method of claim 6 wherein the enzyme is an enzyme catalyzing a biochemical reaction in which hydrogen peroxide is formed, or in which the pH is changed.

9. Method of claim 8 wherein the enzyme is an enzyme catalyzing a biochemical reaction in which hydrogen peroxide is formed, and the enzyme is glucose oxidase or alcoholase.

10. Method of claim 1 wherein the combination aqueous solution is a solution in water or in saline of 0.9% by weight of NaCl, comprising 0.5 to 12% by weight of the hydrogel forming polymer and, based upon 100 parts by weight of the hydrogel forming polymer, 1 to 3 parts by weight of the polyazonium compound, 0.5 to 10 parts by weight of glutardialdehyde, and up to 20 parts by weight of heparin or up to 10 parts by weight of glucose oxidase as the biochemically active material.

11. Method of claim 10 wherein the combination aqueous solution is a solution in water or in saline of 0.9% by weight of NaCl, comprising 0.5 to 12% by weight of the hydrogel forming polymer and, based upon 100 parts by weight of the hydrogel forming polymer, 2 to 2.5 parts by weight of the polyazonium compound, 5 to 8.5 parts by weight of glutardialdehyde, and 2 to 15 parts by weight of heparin as the biochemically active material.

12. Method of claim 10 wherein the combination aqueous solution is a solution in water or in saline of 0.9% by weight of NaCl, comprising 0.5 to 12% by weight of the hydrogel forming polymer and, based upon 100 parts by weight of the hydrogel forming polymer, 2 to 2.5 parts by weight of the polyazonium compound, 5 to 8.5 parts by weight of glutardialdehyde, and 2 to 4 parts by weight of glucose oxidase as the biochemically active material.

13. Method of claim 10 wherein the combination aqueous solution comprises 5 to 9% by weight of the hydrogel forming polymer.

14. Method of claim 10 wherein the combination aqueous solution comprises about 7% by weight of the hydrogel forming polymer.

15. Method of claim 1 wherein the substrate is part of a biochemical sensor.

16. Method of claim 15 wherein the substrate is made of non-conductive material.

17. Method of claim 16 wherein the substrate is made of silicon, alumina, silica or glass.

18. Method of claim 15 wherein the substrate is first provided with a base layer by applying an aqueous solution comprising a photosensitive hydrogel forming polymer, and a polyazonium compound and glutardialdehyde as cross linking agents, to form a base coating on the substrate, and thereafter coating onto the base coating said combination aqueous solution.

19. Method of claim 18 wherein the aqueous solution used to form the base layer is a solution in water or in saline of 0.9% by weight of NaCl, comprising 0.5 to 12% by weight of the hydrogel forming polymer and, based upon 100 parts by weight of the hydrogel forming polymer, 2 to 3 parts by weight of the polyazonium compound and >0.5 by weight of glutardialdehyde.

* * * * *